(12) United States Patent
Al-Qaisi et al.

(10) Patent No.: US 10,557,700 B2
(45) Date of Patent: Feb. 11, 2020

(54) DYNAMIC MODE SWITCHING FOR MULTI-MODE OPHTHALMIC OPTICAL COHERENCE TOMOGRAPHY

(71) Applicant: Novartis AG, Basel (CH)

(72) Inventors: Muhammad K Al-Qaisi, Ladera Ranch, CA (US); Guy Holland, San Juan Capistrano, CA (US)

(73) Assignee: Novartis AG, Basel (CH)

( * ) Notice: Subject to any disclaimer, the term of this patent is extended or adjusted under 35 U.S.C. 154(b) by 29 days.

(21) Appl. No.: 15/869,849

(22) Filed: Jan. 12, 2018

(65) Prior Publication Data

US 2018/0209778 A1   Jul. 26, 2018

Related U.S. Application Data

(60) Provisional application No. 62/474,698, filed on Mar. 22, 2017, provisional application No. 62/449,645, filed on Jan. 24, 2017.

(51) Int. Cl.
*G01B 9/02* (2006.01)
*A61B 3/00* (2006.01)
*A61B 3/10* (2006.01)

(52) U.S. Cl.
CPC ........ *G01B 9/02091* (2013.01); *A61B 3/0025* (2013.01); *A61B 3/102* (2013.01); *G01B 9/02004* (2013.01); *G01B 9/02043* (2013.01)

(58) Field of Classification Search
CPC .... G01B 9/02091; G01B 9/02004; H01S 5/00
See application file for complete search history.

(56) References Cited

U.S. PATENT DOCUMENTS

| | | | |
|---|---|---|---|
| 6,452,518 B1 | 9/2002 | Kawabata | |
| 9,709,379 B2* | 7/2017 | Kemp | G01B 9/02004 |
| 2010/0182182 A1 | 7/2010 | Kiang et al. | |
| 2013/0120757 A1 | 5/2013 | Yu et al. | |
| 2013/0271772 A1* | 10/2013 | Johnson | G01B 9/02004 |
| | | | 356/479 |
| 2013/0301000 A1* | 11/2013 | Sharma | A61B 3/102 |
| | | | 351/206 |
| 2014/0268038 A1 | 9/2014 | Schmoll | |
| 2017/0065169 A1* | 3/2017 | Fukasawa | A61B 3/102 |

* cited by examiner

*Primary Examiner* — Jonathan M Hansen

(57) ABSTRACT

Techniques and apparatus for selectively producing half-depth and full-depth OCT images, based on a swept-source OCT interference signal. An example method comprises selecting from a first sampling rate and a second sampling rate, the second sampling rate being twice the first sampling rate, and sampling the swept-source Optical Coherence Tomography (OCT) interference signal at the selected sampling rate, using a k-clock signal having a frequency range corresponding to the first sampling rate, to produce a sampled OCT interference signal. The method further comprises processing the sampled OCT interference signal to obtain an OCT image, such that the resulting OCT image is a half-depth image in the event the first sampling rate is selected and a full-depth image in the event the second sampling rate is selected.

4 Claims, 6 Drawing Sheets

DYNAMIC MODE SWITCHING FOR MULTI-MODE OPHTHALMIC OPTICAL COHERENCE TOMOGRAPHY

TECHNICAL FIELD

The present disclosure is generally related to Optical Coherence Tomography (OC), such as is used in ophthalmic applications, and is more particularly related to techniques and apparatus for selectively producing half-depth and full-depth OCT images, using mode-switching circuits.

BACKGROUND

Optical Coherence Tomography (OCT) is a technology used to perform high-resolution cross sectional imaging. It is often applied to imaging biological tissue structures, such as the human eye, for example, on microscopic scales in real time. Optical waves are reflected from an object or sample and a computer produces images of cross sections or three-dimensional volume renderings of the sample by using information on how the waves are changed upon reflection.

OCT may be performed based on time-domain processing of Fourier-domain processing. The latter approach includes a technique known as swept-source OCT, where the spectral components of the optical signal used to illuminate the sample are encoded in time. In other words, the optical source is swept (or stepped) across an optical bandwidth, with the interference signal produced by the combination of the source signal and the reflected signal being sampled at several points across this optical bandwidth. The sampling clock, which is typically designed to sample the interference signal at equally spaced points across the optical bandwidth, is referred to as a "k-clock," and the resulting samples, which are samples in the optical frequency domain or "k-space," are referred to as "k-space" samples.

In practice, the optical source is successively directed to each of a series of points on the surface of the object (e.g., the eye) being imaged, with k-space samples across the spectral bandwidth being collected at each of these points. The k-space samples corresponding to each point are processed, using well-known digital signal processing techniques, to provide image data corresponding to a range of depths in the imaged object, i.e., an "A-scan." The A-scans across the series of points are compiled to create a B-scan; multiple B-scans, corresponding to sequential "rows" along the imaged object can be compiled to form three-dimensional image data. It will be appreciated that because of the Fourier-domain processing used in swept-source OCT, z-axis scanning, where the length of the reference arm of the interference is successively changed to obtain information at different depths in the imaged object, is not needed. Rather, depth information is obtained from the processing of the k-space samples, over a range of depths that corresponds inversely to the size of the spectral frequency increments for the k-space samples.

SUMMARY

Described in detail below are several techniques and apparatus for selectively producing half-depth and full-depth OCT images, based on a swept-source OCT interference signal and, at least in some embodiments, using mode-switching circuitry.

An example method according to some embodiments, comprises selecting from a first sampling rate and a second sampling rate, the second sampling rate being twice the first sampling rate, and sampling the swept-source Optical Coherence Tomography (OCT) interference signal at the selected sampling rate, using a k-clock signal having a frequency range corresponding to the first sampling rate, to produce a sampled OCT interference signal. The method further comprises processing the sampled OCT interference signal to obtain an OCT image, such that the resulting OCT image is a half-depth image in the event the first sampling rate is selected and a full-depth image in the event the second sampling rate is selected.

In some embodiments, sampling the swept-source OCT interference signal comprises using the k-clock signal to sample the swept-source OCT interference signal in either a half-rate mode or a full-rate mode, based on whether the first sampling rate or second sampling rate is selected, where the half-rate mode comprises sampling the swept-source OCT interference signal on either every rising edge of the k-clock signal or every falling edge of the k-clock signal, but not both, and where the full-rate mode comprises sampling the swept-source OCT interference signal on every rising edge and every falling edge of the k-clock signal. In other embodiments, sampling the swept-source OCT interference signal at the selected sampling rate comprises, in the event the first sampling rate is selected, sampling the swept-source OCT interference signal using a first A/D converter and the k-clock signal, to obtain the sampled OCT interference signal, and, in the event the second sampling rate is selected, sampling the swept-source OCT interference signal using the first A/D converter and the k-clock signal, to obtain a first sampled output at the first rate, and also sampling the swept-source OCT interference signal using a second A/D converter and a phase-shifted replica of the k-clock signal, in parallel with sampling the swept-source OCT interference signal using the first A/D converter, to obtain a second sampled output at the first rate, the resulting second sampled output is shifted in time relative to the first sampled output. In these embodiments, the first and second sampled outputs are combined, to obtain the sampled OCT interference signal. In some of these embodiments, the phase-shifted replica of the k-clock signal is selectively generated, i.e., in the event the second sampling rate is selected.

Apparatus for carrying out one or more of the techniques summarized above are also described in detail below. An example is an Optical Coherence Tomography (OCT) data acquisition and processing circuit configured to selectively produce a half-depth OCT image or a full-depth OCT image based on a swept-source OCT interference signal, where the OCT data acquisition and processing circuit comprises an analog-to-digital (A/D) converter circuit configured to selectively sample the swept-source OCT interference signal at a first sampling rate or a second sampling rate, using a k-clock signal, to produce a sampled OCT interference signal, where the second sampling rate is twice the first sampling rate and where the sampling at the first sampling rate or a second sampling rate is based on a rate selection signal. The example OCT data acquisition and processing circuit further comprises a digital signal processing circuit configured to process the sampled OCT interference signal to obtain an OCT image, such that the OCT image is a half-depth image in the event the first sampling rate is selected and a full-depth image in the event the second sampling rate is selected.

In some embodiments, the A/D converter circuit in the example OCT data acquisition and processing circuit summarized above comprises a dual-rate A/D converter configured to produce the sampled OCT interference signal by sampling the swept-source OCT interference signal, using the k-clock signal, in either a half-rate mode or a full-rate mode, responsive to the rate selection signal, where the half-rate mode comprises sampling the swept-source OCT interference signal on either every rising edge of the k-clock signal or every falling edge of the k-clock signal, but not both, and where the full-rate mode comprises sampling the swept-source OCT interference signal on every rising edge and every falling edge of the k-clock signal.

In other embodiments, the A/D converter circuit in the example OCT data acquisition and processing circuit summarized above instead comprises a k-clock doubler circuit configured to generate first and second A/D clock signals from the k-clock signal, the first A/D clock signal being a replica of the k-clock signal and the second A/D clock signal being a phase-shifted replica of the k-clock signal, and first and second A/D converters, each being configured to receive the swept-source OCT interference signal, and each being configured to selectively sample the swept-source OCT interference signal using the first and second A/D clock signals, respectively, to produce respective sampled outputs. The A/D converter circuit in these embodiments further comprises a multiplexer configured to combine the sampled outputs to produce the sampled OCT interference signal. The A/D converter circuit in these embodiments is configured to operate in either a half-rate mode or a full-rate mode, responsive to the rate selection signal, where only one of the A/D converters is activated in the half-rate mode and both of the A/D converters are activated in the full-rate mode. In some of these embodiments, the k-clock doubler circuit is configured to selectively generate one or both of the first and second A/D clock signals, responsive to the rate selection signal.

It will be understood that the particular methods and devices summarized above and described in detail below as embodying the invention are shown by way of illustration and not as a limitation of the invention. The several principles and features of this invention as detailed herein may be employed in various embodiments without departing from the scope of the invention.

DETAILED DESCRIPTION

In ophthalmic applications, low-coherence interferometry techniques, like OCT, are used to provide information about spacing of eye layers. Ophthalmic biometry requires measuring anatomical and optical parameters from the anterior segment of the eye, as well as measurements performed on the full-eye length. However, measuring the full length of the eye requires certain performance tradeoffs, relative to performing anterior segment measurements, which require a shorter depth of measurement.

Several methods have been demonstrated to allow an OCT system to image both the anterior chamber of the eye and the full eye. These methods involve, for example, using long optical delays or dual optical delays, performing numerical resampling, removing mirror-image ambiguity in the digital signal processing of the OCT data, removing mirror-image ambiguity from the OCT data, or unfolding of the aliased component of the image from the OCT data. Each of these methods, however, requires a compromise in either system performance or impacts the system design constraints.

In swept-source OCT (SSOCT), the choice of k-clock period, which corresponds to the sample step size in the optical frequency domain, affects the OCT imaging performance. Generally speaking, imaging across a greater depth in the sample, such as the human eye, requires a higher sampling rate, which corresponds to a finer step size in the optical bandwidth.

Embodiments of the present invention provide the capability for OCT systems sampled in the spectral domain, i.e., so-called swept-source OCT systems, or SSOCT systems, to support dynamic switching of the ranging depth, e.g., by selectively sampling the k-clock period multiple times. This allows the imaging depth to be extended with a simple digital software switch of the digital acquisition board and the laser sweep rate. With the techniques and devices described herein, the sampling of the raw OCT data can be manipulated so as to provide fast adjustment of the ranging depth, without the need for multiple clock generators or opto-mechanical switching mechanisms. The simultaneous measurements are provided without compromising the spatial resolution of the processed OCT images.

Figure 9:
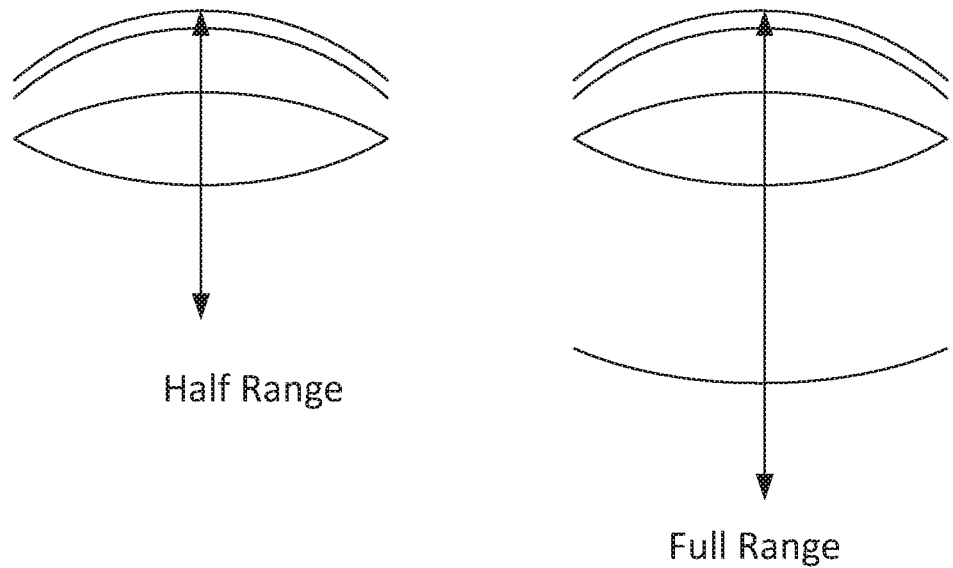
FIG. 9 illustrates example half-range and full-range OCT images.
Figure 9:
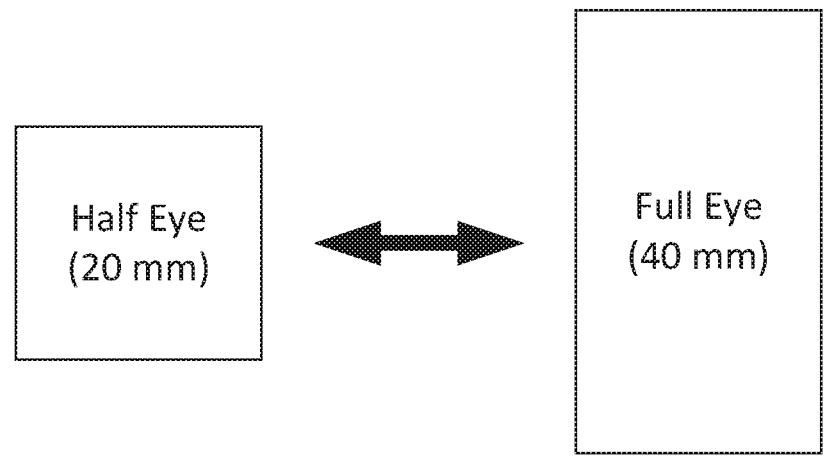

The techniques and apparatus described herein are particularly useful for ophthalmic imaging and biometry, where they may be used to selectively provide half-range or full-range images of the eye, for different ophthalmic applications. A full-range image may have a depth range of about 40 millimeters, for example, allowing imaging of the full depth of the eye, while a half-range image may have a depth range of about 20 millimeters, for example, allowing imaging of the anterior segment of the eye. An example of a full-range image and a corresponding example of a half-range image are shown in FIG. 9. In FIG. 9, a full range image measures the complete axial length of the eye over a ranging depth, in this case, of 40 mm. A half range image measures the anterior chamber of the eye over a ranging depth, in this case, of 20 mm. In FIG. 9, the half-range image includes an image of the cornea and lens, while the full-range image includes an image of the cornea, lens and retina. Generally, the half-range image may be used to determine dimensions associated with the anterior chamber of the eye, such as corneal thickness and curvature, lens thickness and curvature, and anterior chamber depth, while the full-range image may be used to determine dimensions such as axial length of the eye.

Figure 1:
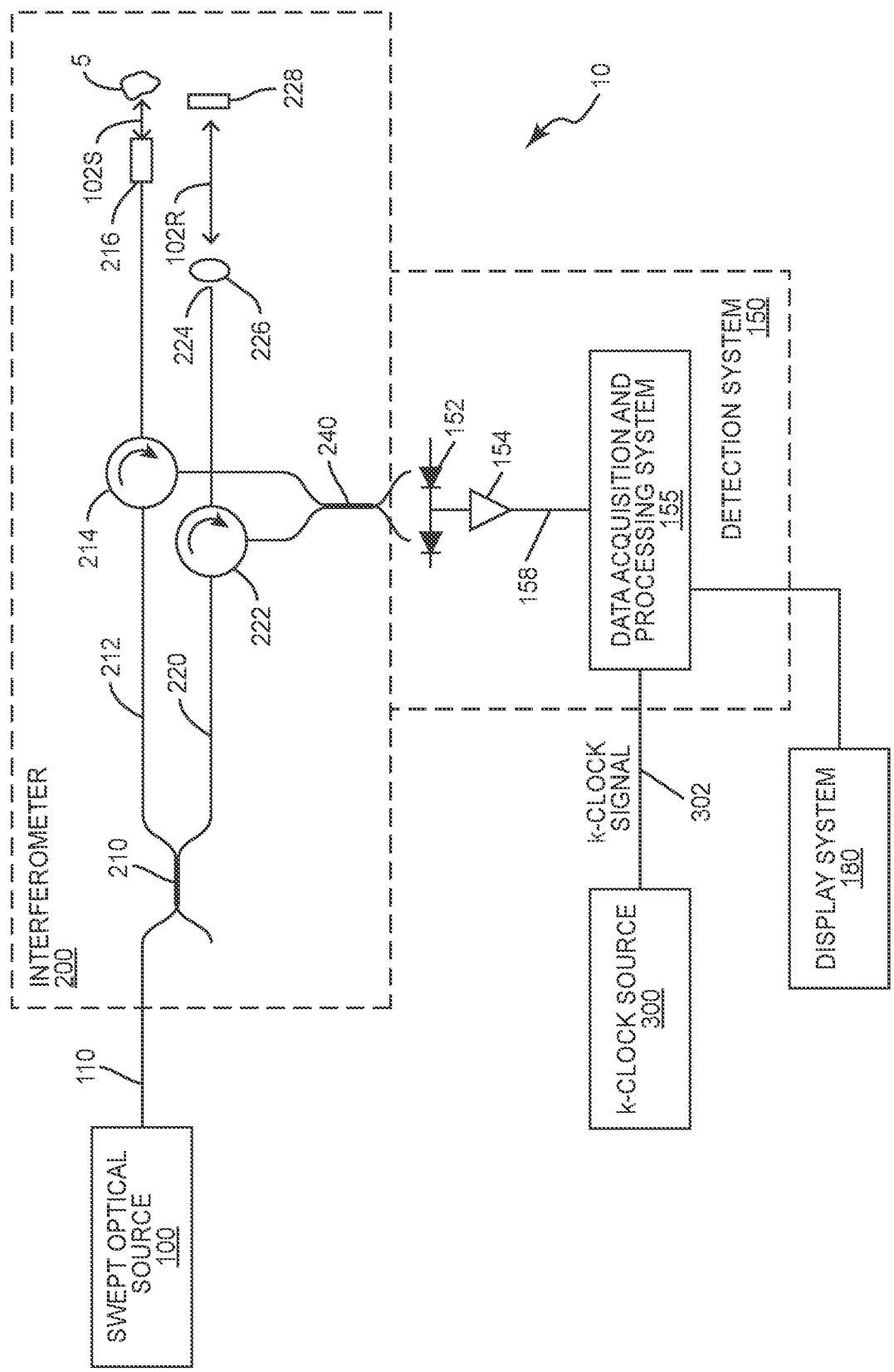
FIG. 1 illustrates components of an example swept-source Optical Coherence Tomography (OCT) system.

To provide context for the detailed description of these techniques that follows, FIG. 1 is first described. FIG. 1 illustrates an example SSOCT system 10, which comprises a swept optical source 100, an interferometer 200, a detection system 150, a k-clock source 300, and a display system 180. It will be appreciated that the details shown here are an example only; other systems may vary in well-known ways.

Swept optical source 100 is typically designed for wavelength tuning, to generate swept optical signals that repeatedly scan over a predetermined optical tuning range, e.g., over a range of 100 nm or greater, at a scanning repetition rate of 1 kilohertz (kHz) or greater. The scanning repletion rate (also referred to as "laser sweep rate" or "sweep rate") is the rate at which the laser makes a full sweep through the range of wavelengths. For example, if the laser has a central wavelength of 1060 nm and is swept over a range of 100 nm (i.e. from 1010 nm to 1110 nm), the sweep rate is the rate over which the 100 nm range of wavelengths is swept. When the sweep rate is 1 kilohertz, the 100 nm range of wavelengths is swept in 1 microsecond (i.e. a thousand times a second). k-clock source 300 is configured to generate k-clock signals at equally spaced optical frequency sampling intervals, as the output from swept optical source 100 is swept over the source's tuning range. Interferometer 200, in this particular example is implemented as a Mach-Zehnder-type interferometer designed for operation at, for example, at optical wavelengths around 1060 nm or 1310 nm. This interferometer is used to analyze the optical signals reflected from the imaged object 5, which may be a human eye. It will be appreciated that interferometer 200 may be based on a different design when designed for different wavelengths such as central wavelengths of 1060 nm or 830 nm. In one example, the central wavelength of the swept optical source 100 is 1060 nm, and the swept optical source 100 is swept over a 100 nm range.

As seen in the figure, the swept optical output from the swept optical source 100 is coupled to an optical fiber coupler 210 in interferometer, via optical fiber 110. Optical fiber coupler 210 may be a 90/10 optical fiber coupler, for example. The swept optical signal is divided by the coupler 210 between a reference arm 220 and a sample arm 212.

The optical fiber of the reference arm 220 terminates at a fiber end-face 224. The light 102R exiting from the reference arm fiber endface 224 is collimated by a lens 226 and reflected by a mirror 228, in the illustrated implementation. Mirror 228 has an adjustable fiber-to-mirror distance, in one example. This distance determines a reference point in the depth range being imaged, i.e., the position in the sample 5 of the zero-path length difference between the reference arm 220 and the sample arm 212. This distance can be adjusted, in some embodiments, for different sampling probes and/or imaged samples. Light returning from the reference mirror 228 is returned to a reference arm circulator 222 and directed to a 50/50 fiber coupler 240.

The fiber on sample arm 212 terminates at the sample arm probe 216. The exiting swept optical signal 102S is focused by the probe 216 onto the sample 5. Light returning from the sample 5 is returned to a sample arm circulator 214 and directed to the 50/50 fiber coupler 240. The reference arm signal and the sample arm signal are combined in the fiber coupler 240 to generate an optical interference signal.

The optical interference signal is detected and processed in detection system 150. Specifically, in the implementation shown in FIG. 1, a balanced receiver, comprising two optical detectors 152, is located at each of the outputs of the fiber coupler 240. The electronic interference signal from the balanced receiver 152 is amplified by amplifier 154, to produce an interference signal 158 for processing by data acquisition and processing system 155.

Data acquisition and processing system 155 of the detection system 150 is used to sample the interference signal output from the amplifier 154. The k-clock signal from the k-clock source 300 is used by the data acquisition system 155 to synchronize system data acquisition with the frequency tuning of the optical swept source system 100. Note that because the optical tuning of the optical swept source system 100 may not be linear, with respect to time, the k-clock signal may have irregular periods and thus does not have a fundamental frequency, but rather a frequency range, characterized by an average frequency that may be regarded as a sampling rate.

Typically, once a complete data set has been collected of the sample 5 by spatially raster-scanning the focused probe beam point over the sample, e.g., in an x-y, fashion or in a theta-z fashion, so that the spectral response at each one of these points is generated from the frequency tuning of the swept optical source 100, the data acquisition and processing system performs a Fourier transform on the data, according to well-known techniques, in order to reconstruct the image and perform a 2D or 3D tomographic reconstruction of the sample 5. The information generated by the data acquisition and processing can then be displayed with display system 180, such as a video monitor.

Figure 2:
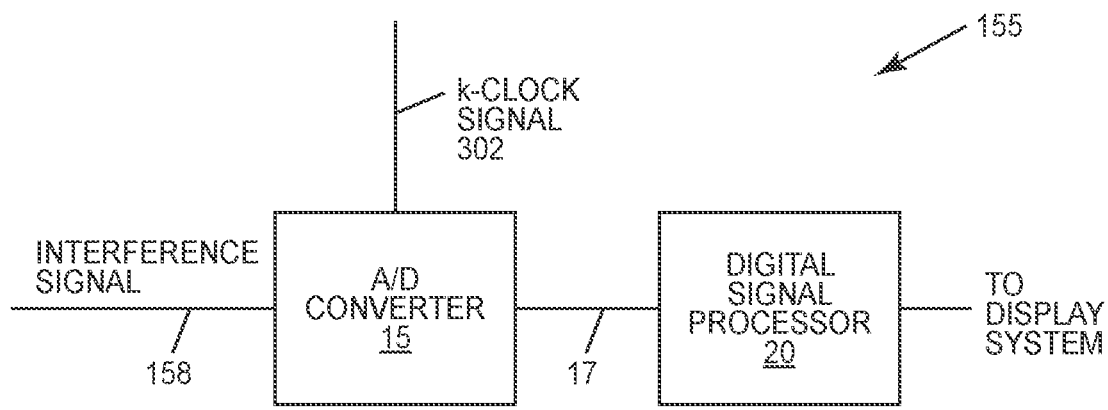
FIG. 2 is a block diagram illustrating components of a conventional digital acquisition and processing circuit.

FIG. 2 illustrates further details of an example data acquisition and processing system 155. At the level pictured, the illustrated data acquisition and processing system 155 is consistent with conventional techniques, as well as with the inventive techniques to be described in further detail below. As seen in the figure, data acquisition and processing system 155 comprises an analog-to-digital (A/D) converter, configured to sample interference signal 158 using the k-clock signal 302 as a sampling clock. This produces a sampled OCT signal, on sampling channel 17, which is supplied to a digital signal processor circuit 20 for Fourier processing and image reconstruction.

Figure 3:
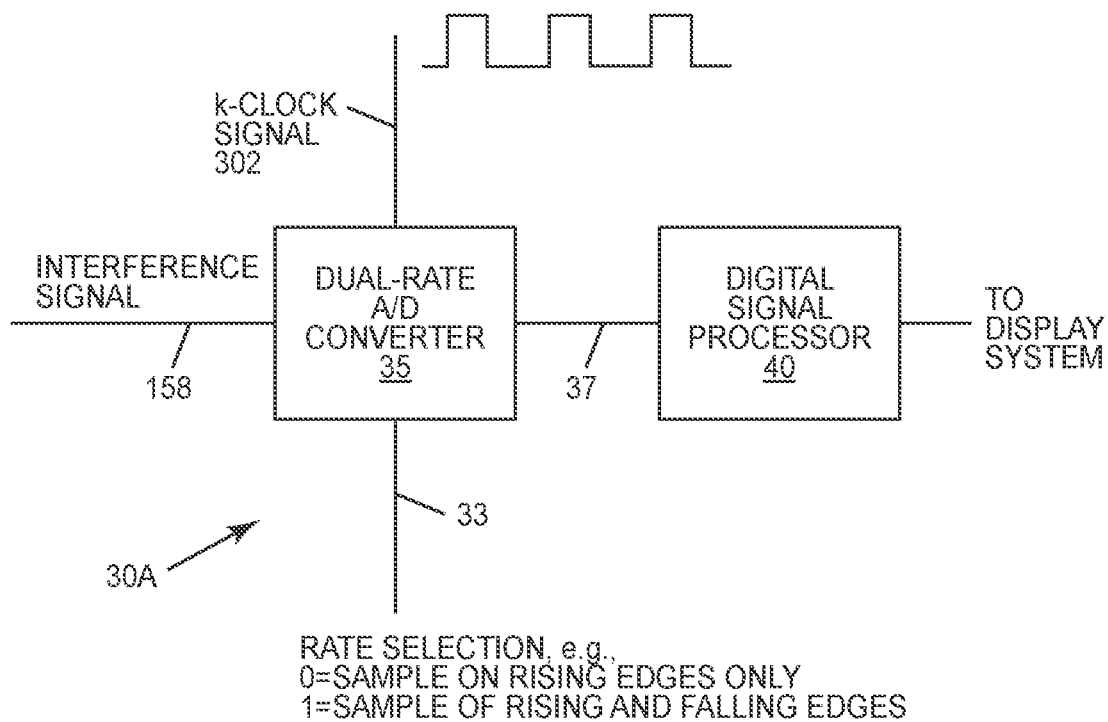
FIG. 3 illustrates components of an example digital acquisition and processing circuit consistent with some embodiments of the presently disclosed invention.

FIG. 3 illustrates an example data acquisition and processing system 30A, consistent with some embodiments of the present invention. Data acquisition and processing system 30A can be substituted for data acquisition and processing system 155 in the system of FIG. 1, but may also be used in other SSOCT systems.

Data acquisition and processing system 30A comprises a dual-rate A/D converter which, like A/D converter 15 in FIG. 2, is configured to sample interference signal 158 using the k-clock signal as a sampling clock. However, unlike the A/D converter of FIG. 2, dual-rate A/D converter 35 is configured to produce a sampled OCT interference signal, on sampling channel 37, by sampling the swept-source OCT interference signal 158, using the k-clock signal, in either a half-rate mode or a full-rate mode, responsive to a rate selection signal. When operated in the half-rate mode, e.g., as selected by a value of "0" for the rate selection input, the dual-rate A/D converter 35 samples the swept-source OCT interference signal on either every rising edge of the k-clock signal or every falling edge of the k-clock signal, but not both. When operated in the full-rate mode, e.g., as selected by a value of "1" for the rate selection input, the dual-rate A/D converter 35 samples the swept-source OCT interference signal on every rising edge and every falling edge of the k-clock signal. Thus, the full-rate mode produces two samples for every period of the k-clock, as compared to one per period for the half-rate mode. It will be appreciated, then, that sampling channel 37 is a dual-rate channel, supporting two different sample bandwidths depending on whether the half-rate mode or the full-rate mode is selected, where selecting the half-rate mode or the full-rate mode is equivalent to selecting a first or second sampling rate (in the k-domain) for sampling the interference signal 158, the second sampling rate being twice the rate of the first.

In another example, both the sampling rate and laser sweep rate are different in half-rate mode and full-rate mode. In general, for half-rate mode, the sampling rate is half of the sampling rate of full-rate mode and the sweep rate is double the sweep rate for full-rate mode. In FIG. 3, data acquisition and processing system 30A comprises a dual-rate A/D converter which, like A/D converter 15 in FIG. 2, is configured to sample interference signal 158 using the k-clock signal as a sampling clock. However, unlike the A/D converter of FIG. 2, dual-rate A/D converter 35 is configured to produce a sampled OCT interference signal, on sampling channel 37, by sampling the swept-source OCT interference signal 158, using the k-clock signal, in either a half-rate mode or a full-rate mode and a selected sweep rate, responsive to a rate selection signal. When operated in the half-rate mode, e.g., as selected by a value of "0" for the rate selection input, the dual-rate A/D converter 35 samples the swept-source OCT interference signal on either every rising edge of the k-clock signal or every falling edge of the k-clock signal, but not both. In addition, the sweep rate of R, for example 2 kHz, is used when operating in half-rate mode. When operated in the full-rate mode, e.g., as selected by a value of "1" for the rate selection input, the dual-rate A/D converter 35 samples the swept-source OCT interference signal on every rising edge and every falling edge of the k-clock signal. In addition, the sweep rate of R/2, for example 1 kHz, is used when operating in full-rate mode. Thus, the full-rate mode produces two samples for every period of the k-clock, as compared to one per period for the half-rate mode. In addition, the laser is swept over its range of wavelengths twice as fast in half-rate mode (at a rate R) as in full-length mode (at a rate R/2). It will be appreciated, then, that sampling channel 37 is a dual-rate channel, supporting two different sample bandwidths depending on whether the half-rate mode or the full-rate mode is selected, where selecting the half-rate mode or the full-rate mode is equivalent to selecting a first or second sampling rate (in the k-domain) for sampling the interference signal 158, the second sampling rate being twice the rate of the first. It will also be appreciated, then, that sampling channel 37 is a dual-rate channel, supporting two different sweep rates depending on whether the half-rate mode or the full-rate mode is selected, where selecting the half-rate mode or the full-rate mode is equivalent to selecting a first or second sweep rate, the second sweep rate being half the first sweep rate.

Data acquisition and processing circuit 30A further includes, in addition to dual-rate A/D converter 35, a digital signal processing circuit 40. Like digital signal processing circuit 20 in FIG. 2, digital signal processing circuit 40 performs Fourier processing and image reconstruction based on the sampled OCT interference signal provided to it via sampling channel 37, again using well-known techniques. However, digital signal processing circuit 40 selectively produces half-depth OCT images or full-depth OCT images, corresponding to the half-rate and full-rate modes, respectively.

Figure 4:
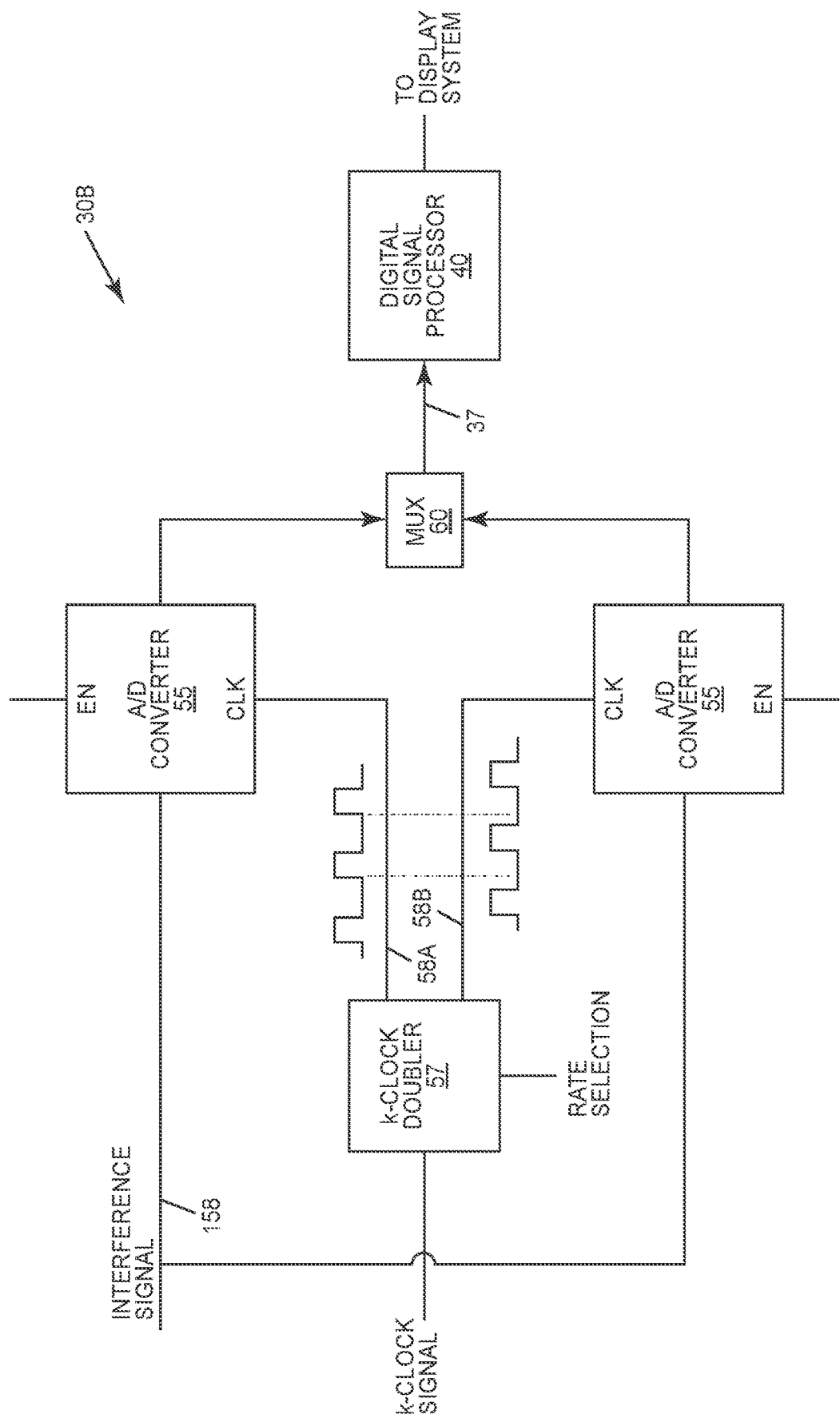
FIG. 4 illustrates components of another example digital acquisition and processing circuit, consistent with other embodiments of the presently disclosed invention.

FIG. 4 illustrates another example of a data acquisition and processing circuit consistent with some embodiments of the presently disclosed invention. As seen in FIG. 4, data acquisition and processing circuit comprises two A/D converters 55, configured in parallel such that each is configured to separately sample interference signal 158. The clock (CLK) inputs to the first and second A/D converters, respectively, are driven by two different replicas of the k-clock signal, shown in the figure as clock signals 58A and 58B, respectively, with one clock signal (58B) being phase-shifted, i.e., delayed, with respect to the other (58A). In the illustrated example, this phase shift is approximately 180 degrees, although different phase shifts may be employed, e.g., to provide a uniform sampling interval in the k-domain. The first and second k-clock signals 58A and 58B are generated in the circuit shown in FIG. 4 by k-clock doubler circuit 57. The outputs of the first and second A/D converters 55 are combined, with a multiplexer (MUX) 60, to produce a sampled OCT interference signal supplied to digital signal processor circuit 40 via sampling channel 37. As was the case in the circuit shown in FIG. 3, digital signal processing circuit 40 performs Fourier processing and image reconstruction based on the sampled OCT interference signal provided to it via sampling channel 37, again using well-known techniques, to selectively produce half-depth OCT images or full-depth OCT images, corresponding to the half-rate and full-rate modes, respectively.

When data acquisition and processing circuit 30B is operated in full-rate mode, both A/D converters 55 are activated, e.g., via the enable (EN) inputs to the A/D converter circuits 55. Because of the out-of-phase sampling clocks provided to A/D converter circuits, the samples will be taken at interleaved frequency intervals in the k-domain. The multiplexer 60 interleaves these samples, by combining them in the order received, to produce the full-rate sampled OCT interference signal.

In another example, both the sampling rate and laser sweep rate are different in half-rate mode and full-rate mode. In general, for half-rate mode, the sampling rate is half of the sampling rate of full-rate mode and the sweep rate is double the sweep rate for full-rate mode. When data acquisition and processing circuit 30B is operated in full-rate mode, both A/D converters 55 are activated, e.g., via the enable (EN) inputs to the A/D converter circuits 55. Because of the out-of-phase sampling clocks provided to A/D converter circuits, the samples will be taken at interleaved frequency intervals in the k-domain. The multiplexer 60 interleaves these samples, by combining them in the order received, to produce the full-rate sampled OCT interference signal. In addition, in full-rate mode, a sweep rate R/2 of the swept source laser is used (i.e. the sweep rate of the laser in full-rate mode is half the sweep rate of half-rate mode).

When data acquisition and processing circuit 30B is operated in half-rate mode, only one of the A/D converters 55 is activated. This can be done with the enable (EN) inputs, e.g., by setting one to "0" and the other to "1," in some embodiments. In other embodiments, the multiplexer 60 can be controlled so that it only accepts inputs from one of the A/D converters. In still other embodiments, one A/D converter 55 can be effectively inactivated by suppressing its clock signal, e.g., by deactivating one output from k-clock doubler circuit 57, under the control of a rate selection input. Thus, the k-clock doubler circuit 57 is configured, in some embodiments, to selectively generate one or both of the first and second ND clock signals 58A and 58B, responsive to the rate selection signal. Note that this latter approach may be combined with controlling the enable inputs of A/D converters 55 so that only one is activated, in some embodiments.

As noted above, data acquisition and processing circuits 30A and 30B may be substituted for data acquisition and processing circuit 155 in the SSOCT system 10 shown in FIG. 1. More generally, of course, either of these circuits and variations thereof may be included in any of a wide variety of SSOCT systems, such that data acquisition and processing circuit 30A or 30B is combined with a swept optical source and an interferometer coupled to an output of the swept optical source, where the interferometer comprises a detector circuit configured to generate the swept-source OCT interference signal 158 from an optical interference signal produced by the interferometer.

Figure 5:
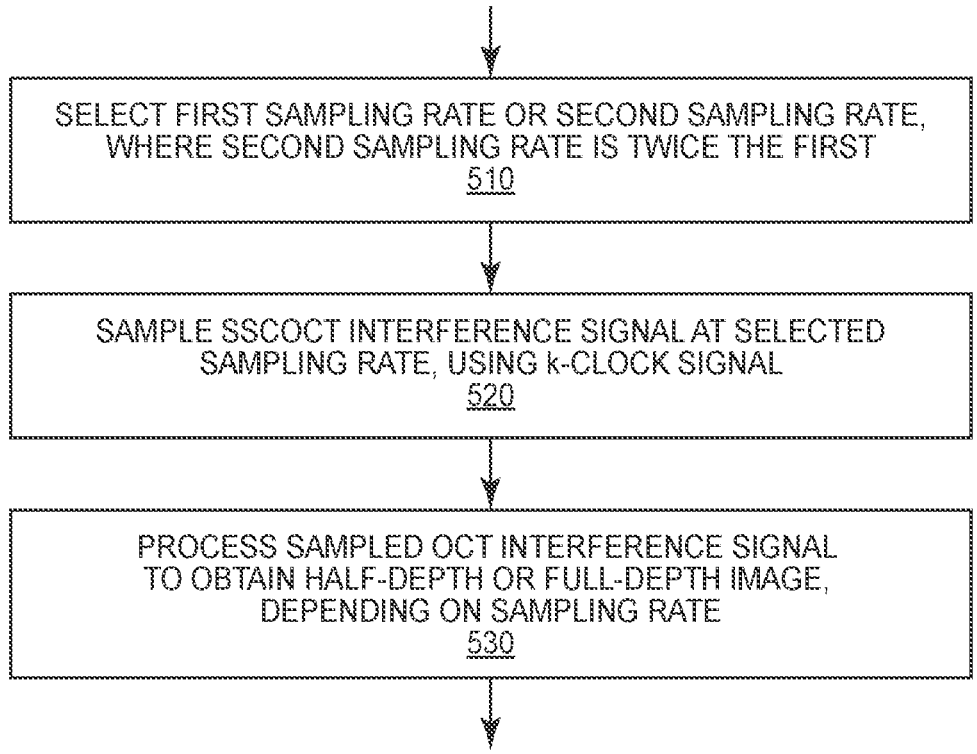
FIG. 5 is a process flow diagram illustrating an example method consistent with embodiments of the present invention.

With the above details in mind, it will be appreciated that FIG. 5 is a process flow diagram illustrating an example method for selectively producing a half-depth OCT image or a full-depth OCT image, based on a swept-source OCT interference signal. As seen at block 510, the method includes selecting from a first sampling rate and a second sampling rate, the second sampling rate being twice the first sampling rate. As shown at block 520, the swept-source Optical Coherence Tomography (OCT) interference signal is then sampled at the selected sampling rate, using a k-clock signal having a frequency range corresponding to the first sampling rate, to produce a sampled OCT interference signal. The sampled OCT interference signal is then processed to obtain an OCT image, such that the OCT image is a half-depth image in the event the first sampling rate is selected and a full-depth image in the event the second sampling rate is selected, as shown at block 530.

In some embodiments, the sampling of the swept-source OCT interference signal (as shown at block 520) comprises using the k-clock signal to sample the swept-source OCT interference signal in either a half-rate mode or a full-rate mode, based on whether the first sampling rate or second sampling rate is selected, wherein the half-rate mode comprises sampling the swept-source OCT interference signal on either every rising edge of the k-clock signal or every falling edge of the k-clock signal, but not both, and wherein the full-rate mode comprises sampling the swept-source OCT interference signal on every rising edge and every falling edge of the k-clock signal.

Figure 6:
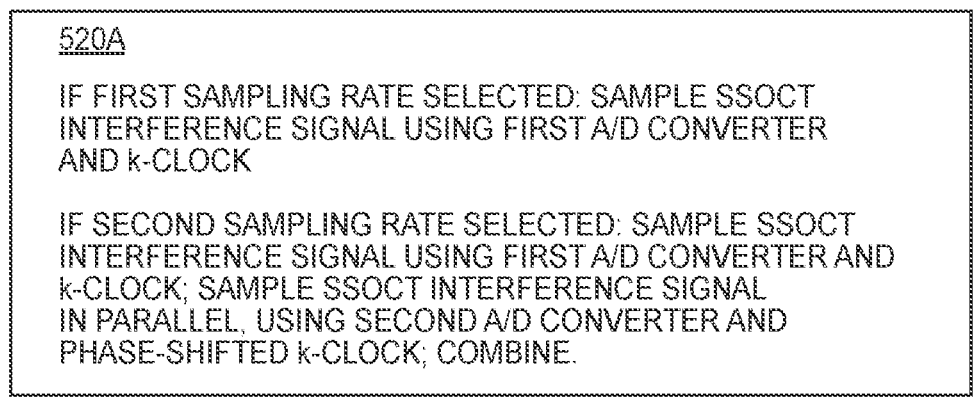
FIG. 6 is a process flow diagram illustrating details of a step from the process flow diagram, according to some embodiments of the present invention.

In other embodiments, the sampling of the swept-source OCT interference signal at the selected sampling rate comprises: in the event the first sampling rate is selected, sampling the swept-source OCT interference signal using a first A/D converter and the k-clock signal, to obtain the sampled OCT interference signal; and, in the event the second sampling rate is selected, sampling the swept-source OCT interference signal using the first A/D converter and the k-clock signal, to obtain a first sampled output at the first rate, and also sampling the swept-source OCT interference signal using a second A/D converter and a phase-shifted replica of the k-clock signal, in parallel with sampling the swept-source OCT interference signal using the first A/D converter, to obtain a second sampled output at the first rate, the second sampled output being shifted in time relative to the first sampled output, and combining the first and second sampled outputs to obtain the sampled OCT interference signal. This alternative is illustrated in FIG. 6, as details in a block 520A. Note that in some of these embodiments, the phase-shifted replica of the k-clock signal may only be selectively generated, i.e., in the event the second sampling rate is selected.

It will be appreciated that the method shown in FIG. 5, when considered in the context of a full SSOCT system, may comprise several other steps and techniques that are not illustrated here. Typically, of course, the steps shown in FIG. 5, which may be carried out in a data acquisition and processing circuit, for example, are carried out in conjunction with the steps of generating the swept-source OCT interference signal using a swept optical source coupled to an interferometer, the interferometer comprising a detector configured to generate the swept-source OCT interference signal from an optical interference signal produced by the interferometer. Display and/or post-processing of the half-depth or full-depth images may be carried out in several embodiments, as well.

Figure 7:
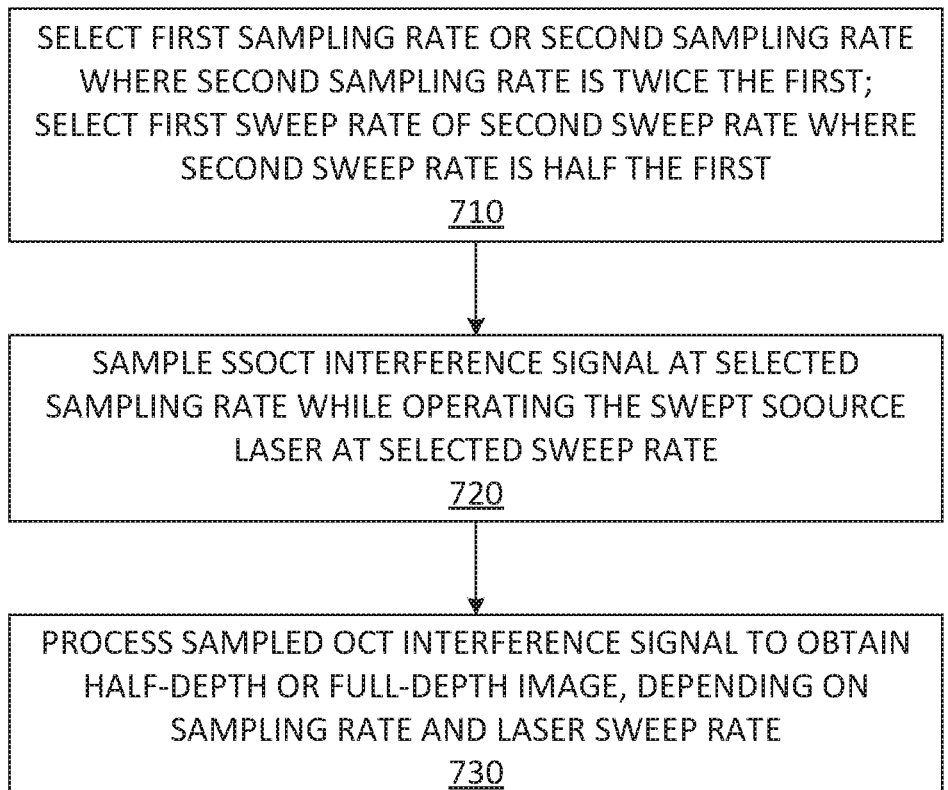
FIG. 7 is a process flow diagram illustrating an example method consistent with embodiments of the present invention.

With the above details in mind, it will be appreciated that FIG. 7 is a process flow diagram illustrating an example method for selectively producing a half-depth OCT image or a full-depth OCT image, based on a swept-source OCT interference signal. As seen at block 710, the method includes selecting from a first sampling rate and a second sampling rate, the second sampling rate being twice the first sampling rate; and selecting from a first laser sweep rate and a second laser sweep rate, the second laser sweep rate being half the first laser sweep rate. As shown at block 720, the swept source laser is operated at the selected sweep rate, while the swept-source Optical Coherence Tomography (OCT) interference signal is then sampled at the selected sampling rate, using a k-clock signal having a frequency range corresponding to the first sampling rate, to produce a sampled OCT interference signal. The sampled OCT interference signal is then processed to obtain an OCT image, such that the OCT image is a half-depth image in the event the first sampling rate and first sweep rate is selected and a full-depth image in the event the second sampling rate and second sweep rate is selected, as shown at block 730.

In some embodiments, the sampling of the swept-source OCT interference signal (as shown at block 720) comprises using the k-clock signal to sample the swept-source OCT interference signal in either a half-rate mode or a full-rate mode, based on whether the first sampling rate or second sampling rate is selected; and simultaneously operating the swept source laser at a first or second sweep rate in either a half-rate mode or a full-rate mode, based on whether the first sweep rate or second sweep rate is selected. In this manner, the half-rate mode comprises sampling the swept-source OCT interference signal on either every rising edge of the k-clock signal or every falling edge of the k-clock signal, but not both, while operating the swept source laser at a first sweep rate R. The full-rate mode comprises sampling the swept-source OCT interference signal on every rising edge and every falling edge of the k-clock signal while operating the swept source laser at a sweep rate of R/2.

Figure 8:
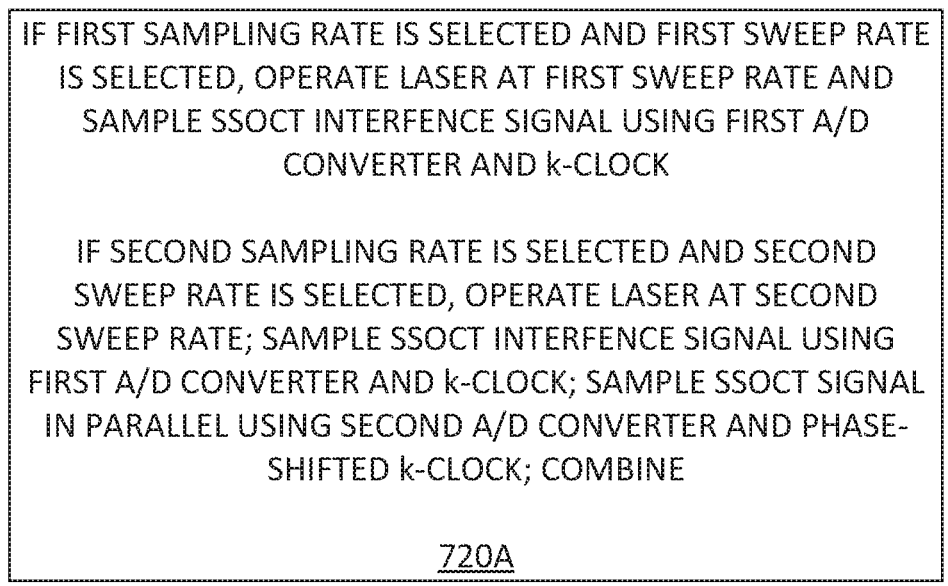
FIG. 8 is a process flow diagram illustrating details of a step from the process flow diagram, according to some embodiments of the present invention.

In other embodiments, the sampling of the swept-source OCT interference signal at the selected sampling rate comprises: in the event the first sampling rate is selected, sampling the swept-source OCT interference signal using a first A/D converter and the k-clock signal, to obtain the sampled OCT interference signal while operating the swept source laser at a first sweep rate; and, in the event the second sampling rate is selected, operating the swept source laser at a second sweep rate, sampling the swept-source OCT interference signal using the first A/D converter and the k-clock signal, to obtain a first sampled output at the first rate, and also sampling the swept-source OCT interference signal using a second A/D converter and a phase-shifted replica of the k-clock signal, in parallel with sampling the swept-source OCT interference signal using the first A/D converter, to obtain a second sampled output at the first rate, the second sampled output being shifted in time relative to the first sampled output, and combining the first and second sampled outputs to obtain the sampled OCT interference signal. This alternative is illustrated in FIG. 8, as details in a block 720A. Note that in some of these embodiments, the phase-shifted replica of the k-clock signal may only be selectively generated, i.e., in the event the second sampling rate is selected.

It will be appreciated that the method shown in FIG. 7, when considered in the context of a full SSOCT system, may comprise several other steps and techniques that are not illustrated here. Typically, of course, the steps shown in FIG. 7, which may be carried out in a data acquisition and processing circuit, for example, are carried out in conjunction with the steps of generating the swept-source OCT interference signal using a swept optical source coupled to an interferometer, the swept optical source being operated at a sweep rate, the interferometer comprising a detector configured to generate the swept-source OCT interference signal from an optical interference signal produced by the interferometer. Display and/or post-processing of the half-depth or full-depth images may be carried out in several embodiments, as well.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for selectively producing a half-depth OCT image or a full-depth OCT image, based on a swept-source OCT interference signal, the method comprising:
   selecting from a first sampling rate and a second sampling rate, the second sampling rate being twice the first sampling rate;
   selecting from a first sweep rate and a second sweep rate the second sweep rate being half the first;
   operating a swept optical source at the selected sweep rate;
   sampling the swept-source Optical Coherence Tomography (OCT) interference signal at the selected sampling rate, using a single k-clock signal having a frequency range corresponding to the first sampling rate, to produce a sampled OCT interference signal, the single k-clock signal produced by a single k-clock; and
   processing the sampled OCT interference signal to obtain an OCT image, such that the OCT image is a half-depth image in the event the first sampling rate is selected and a full-depth image in the event the second sampling rate is selected;
   wherein said sampling the swept-source OCT interference signal comprises using the single k-clock signal from the single k-clock to sample the swept-source OCT interference signal in either a half-rate mode or a full-rate mode, based on whether the first sampling rate or second sampling rate is selected, wherein the half-rate mode comprises sampling the swept-source OCT interference signal on either every rising edge of the single k-clock signal or every falling edge of the single k-clock signal, but not both, and wherein the full-rate mode comprises sampling the swept-source OCT interference signal on every rising edge and every falling edge of the single k-clock signal.

2. The method of claim 1, further comprising generating the swept-source OCT interference signal using the swept optical source coupled to an interferometer, the interferometer comprising a detector configured to generate the swept-source OCT interference signal from an optical interference signal produced by the interferometer.

3. An Optical Coherence Tomography (OCT) data acquisition and processing circuit configured to selectively produce a half-depth OCT image or a full-depth OCT image based on a swept-source OCT interference signal, the OCT data acquisition and processing circuit comprising:
   an analog-to-digital (A/D) converter circuit configured to selectively sample the swept-source OCT interference signal at a first sampling rate or a second sampling rate while operating a swept optical source at a first sweep rate or a second sweep rate, using a single k-clock signal from a single k-clock to produce a sampled OCT interference signal, wherein the second sampling rate is twice the first sampling rate and wherein the sampling at the first sampling rate or a second sampling rate is based on a rate selection signal and further wherein the second sweep rate is half the first sweep rate; and
   a digital signal processing circuit configured to process the sampled OCT interference signal to obtain an OCT image, such that the OCT image is a half-depth image in the event the first sampling rate is selected and a full-depth image in the event the second sampling rate is selected;
   wherein the A/D converter circuit comprises a dual-rate A/D converter configured to produce the sampled OCT interference signal by sampling the swept-source OCT interference signal, using the single k-clock signal, in either a half-rate mode or a full-rate mode, responsive to the rate selection signal, wherein the half-rate mode comprises sampling the swept-source OCT interference signal on either every rising edge of the single k-clock signal or every falling edge of the single k-clock signal, but not both, and wherein the full-rate mode comprises sampling the swept-source OCT interference signal on every rising edge and every falling edge of the single k-clock signal.

4. An OCT system comprising the OCT data acquisition and processing circuit of claim 3, and further comprising:
   the swept optical source;
   an interferometer coupled to an output of the swept optical source, the interferometer comprising a detector circuit configured to generate the swept-source OCT interference signal from an optical interference signal produced by the interferometer.

* * * * *